United States Patent [19]

Ottofrickenstein et al.

[11] Patent Number: 4,622,300

[45] Date of Patent: Nov. 11, 1986

[54] HYDROLYSIS OF LACTOSE IN WHEY

[75] Inventors: Hans Ottofrickenstein, Darmstadt-Elberstadt; Hermann Plainer, Reinheim; Bruno Sprössler; Helmut Uhlig, both of Rossdorf, all of Fed. Rep. of Germany

[73] Assignee: Rohm GmbH Chemische Fabrik, Darmstadt-Elberstadt, Fed. Rep. of Germany

[21] Appl. No.: 589,686

[22] Filed: Mar. 15, 1984

[30] Foreign Application Priority Data

Mar. 23, 1983 [DE] Fed. Rep. of Germany ....... 3310430

[51] Int. Cl.$^4$ ...................... C12P 19/02; A23C 21/02; C12N 11/00; C12N 11/02
[52] U.S. Cl. ..................................... 435/105; 426/41; 435/174; 435/177
[58] Field of Search ................... 426/41, 42; 435/105, 435/264, 174, 177, 288

[56] References Cited

U.S. PATENT DOCUMENTS

| | | | |
|---|---|---|---|
| 4,016,293 | 4/1977 | Coughlin et al. | 426/41 X |
| 4,393,138 | 7/1983 | Baret | 426/41 |
| 4,409,247 | 10/1983 | Baret et al. | 426/41 |
| 4,465,772 | 8/1984 | Hirohara et al. | 426/41 X |

OTHER PUBLICATIONS

Trevan, M. D., Immobilized Enzymes, John Wiley & Sons, N.Y., 1980, pp. 66–70.

*Primary Examiner*—David M. Naff
*Attorney, Agent, or Firm*—Oblon, Fisher, Spivak, McClelland & Maier

[57] ABSTRACT

A process and reactor are disclosed for the continuous treatment of a turbid liquid with a granular treating agent placed in a fixed bed through which the liquid flows. Preferably, the liquid is whey and the treating agent is lactase immobilized on support particles, and treatment involves hydrolysis of lactose in the whey. During treatment, the flow of whey through the fixed bed is periodically interrupted and a flow of cleansing liquid is passed through the fixed bed countercurrent to the flow of whey. The flow of cleansing liquid is under sufficient hydrostatic pressure to press the fixed bed against moving fragmentation devices to separate and fluidize the support particles into a fluidized bed whereby the support particles containing immobilized lactase are cleansed by removing material deposited thereon from the whey.

10 Claims, 1 Drawing Figure

HYDROLYSIS OF LACTOSE IN WHEY

BACKGROUND OF THE INVENTION

1. Field of the Invention

The invention relates to a process for the treatment of turbid liquids, containing finely divided solids, with a granular treating agent which is placed in a fixed bed through which the turbid liquid flows. The invention especially relates to a process for the hydrolysis of the lactose in whey by means of a lactase immobilized on support particles. The support particles loaded with lactase are placed as a fixed bed in a predominantly tubular reactor. As a result, the substrate inhibition which would restrict the conversion of the lactose in a fluidized-bed catalyst is suppressed.

2. Description of the Prior Art

The continuous lactose hydrolysis of lactose by means of a lactase which is bound adsorptively to bead-shaped support particles has been described in DE-OS No. 28 39 737. The process can be performed continuously over several days only if a whey permeate is used from which the natural turbidity has been removed by ultrafiltration.

In the process according to DE-OS No. 31 22 231, the whey is acidified, heated and centrifuged to remove suspended materials. Nevertheless, daily cleansing of the enzyme catalyst is essential in this process, for even following centrifuging there still remain so many colloidally dissolved proreins in the whey that a coating precipitates on the support particles which impairs the activity of the immobilized lactase. For cleaning, the enzyme catalyst, which is placed on a fixed bed, is swirled and flushed with a protease solution that degrades the protein coating and reactivates the lactase.

This process is costly and uneconomical on account of the pretreatment of the whey by heating and centrifuging. However, if unclarifed whey with a turbidity of over 100 NTU is used in this process, then the fixed-bed packing of the enzyme catalyst is gradually transformed into a continuous plug that cannot be swirled and cleansed even by reversing the direction of flow. This phenomenon is primarily observed when the catalyst is frequently re-used.

Therefore, a need continues to exist for a process by which it is possible to continuously treat turbid liquids to convert the same without having to use the prior processing steps of heating and centrifuging. In particular, a need continues to exist for a simple process which permits continuous hydrolysis of lactose in unfiltered whey and which ensures a long enzyme-catalyst life time.

SUMMARY OF THE INVENTION

Accordingly, it is an object of the present invention to provide a process by which it is possible to continuously treat turbid liquids without having to use the prior processing steps of heating or centrifuging.

It is also an object of this invention to provide a process for the continuous treatment of turbid liquids in an economical manner.

Further, it is a particular object of the present invention to provide a process for the continuous hydrolysis of lacrose in unfiltered whey, which ensures a long enzyme-catalyst life time.

According to the present invention, the foregoing and other objects are attained by providing a process for the continuous treatment of a turbid liquid containing finely divided solid substances which entails passing the turbid liquid through a fixed bed of a granular treating agent such that the flow of the turbid liquid through the fixed bed is periodically interrupted and a cleansing liquid is piped through the fixed bed countercurrent to the preceding direction of flow of the turbid liquid, thereby cleansing the granular treating agent of the finely divided solid substances originating from the turbid liquid and also fluidizing and cleansing the granular treating agent in the fluidized bed state, wherein the turbid liquid has a turbidity in excess of 10 NTU and the fixed bed is pressed against mechanically acting fragmentation devices by the hydrostatic pressure of the cleansing liquid, such that the particles of the treating agent are separated from one another and are fluidized into a fluidized bed.

DETAILED DESCRIPTION OF THE PREFERRED EMBODIMENT

Figure 1:
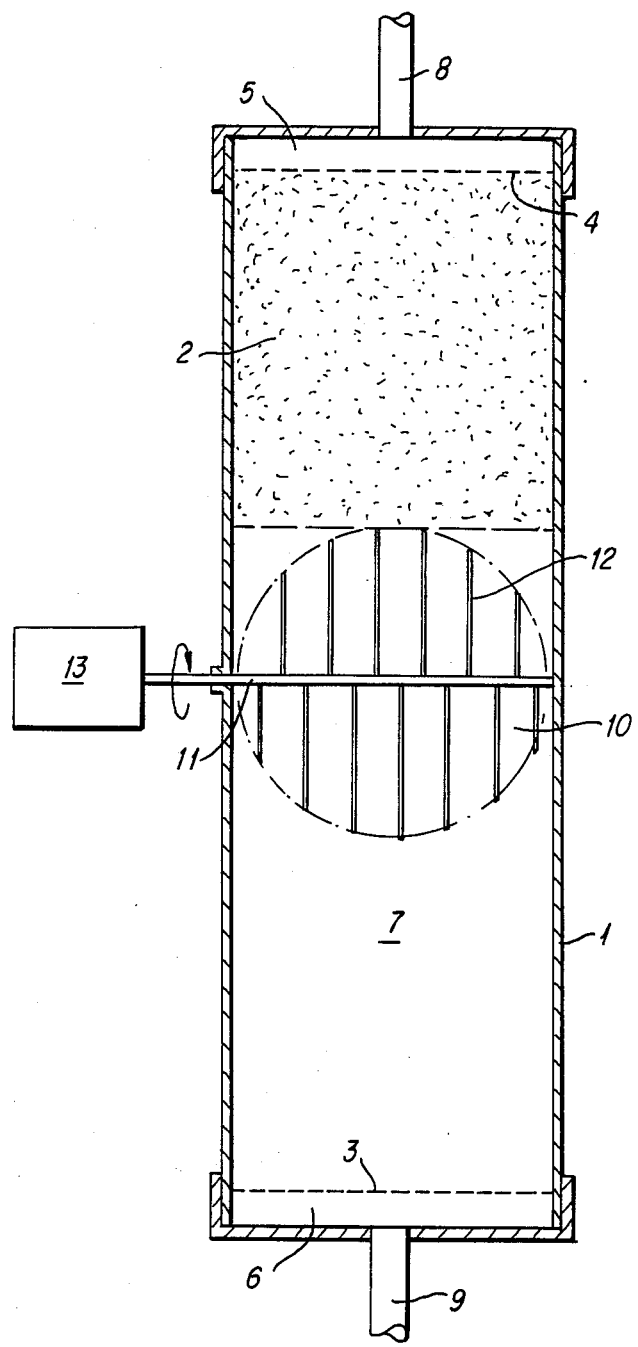
FIG. 1 shows a sectional view of a reactor which is suitable for carrying out the present process. It contains a reaction vessel 1 with a fixed bed 2 of the granular treating agent. The interior space is divided from antechambers 5, 6 on two sides by sieve plates 3 and 4. Area 7 is filled with the inflowing turbid liquid during treatment. The sieve plates 3 and 4 separate the antechambers 5, 6 from the reaction space. Conduits 8 and 9, for introducing and removing liquids or gases, open into the antechambers. Fragmentation devices 10 are installed in the center. A rotary shaft 11 with a majority of projecting blades is suitable as a fragmentation device. Shaft 11 is rotated by a drive 13 that is operated only at the beginning of the cleansing stage, whereby the blades 12 engage the uppermost layer of the fixed bed.

In the flow of the turbid liquid through the fixed bed, tne deposit of the finely divided solids in the interstices of the fixed bed of the granular treating agent cannot be avoided. As a result, the contact surface between the particles of the treating agent gradually becomes smaller and the interaction with the treating agent lessens.

In case of the hydrolysis of whole whey in an enzymatic fixed-bed catalyst, a great loss of effectiveness inevitably occurs after a certain period of operation, depending upon the turbidity content of the whey and upon the nature of the enzyme catalyst particles, linked with an increase in the flow resistance of tne fixed bed and caused by the deposit of the suspended materials from the whey, consisting mainly of milk protein particles in the interstices between the catalyst particles. As long as the catalyst is still rather fresh, the deposits can be largely removed by countercurrent swirling of the fixed bed with an aqueous cleansing liquid and the activity of the catalyst can be restored. After several cleansing cycles there is less and less success with this procedure, so that increasingly shorter times of operation between cleansing cycles must be adopted. In addition, the activity further declines after every cleansing. The danger of microbial contamination increases. The same applies to other enzymatic processes in turbid substrate liquids.

In the process of the invention, the fixed bed, which may be hardened into a continuous plug because of the deposits, is pushed forward into the reaction space like a piston in the cylinder by the hydrostatic pressure of the cleansing liquid and is pressed against fragmentation devices that split the fixed bed into fragements. As soon as the entire fixed bed has been split in this manner, the fragments are swirled in the fluidized bed until they further disintegrate into individual fluidized particles and are freed from adhering deposits. If the fixed bed is not regularly —daily is the best thing—cleansed by mechanical means, so many turbidity particles accumulate on it that the coating of the support in some cases is irreversible. Whey hydrolysis is one of these cases.

The process of the present invention permits a favorable ratio of treatment to cleansing times and thus high productivity. The life of the treating agent is increased because its activity is largely restored in every cycle. It would require a much larger expenditure of time and means if the treating agent were to be removed from the reactor after every cycle and regenerated in a separate device.

These advantages are attained with small additional expenditures for apparatus. Devices to circulate the cleansing liquid through the reaction space are also required for the known method of operation. For the process of the invention they must be designed, if applicable, for the generation of a higher hydrostatic pressure. In the reactor itself, only fragmentation devices are required as additional apparatus components, fragmentation devices which in the simplest case are installed in a fixed position, but preferably are moved by external propulsion, preferably rotating.

The Granular Treating Agent

The granular treating agent can be any finely divided solid material with which a fluid substrate can be treated in a fixed bed. Typical examples are a. Ion exchangers for binding of acids or bases that are dissolved in a liquid substrate;
b. Solid catalysts for the heterogeneous liquid phase conversion of the liquid substrate or components dissolved therein;
c. Adsorbents for binding dissolved components from the liquid substrate;
d. Adsorbents for chromatographic separation of a mixture of components of the liquid substrate;
e. Enzymes immobilized on support particles for enzymatic conversion of dissolved components of the liquid substrate;
f. Biologically active substances immobilized on support particles for affinity chromatography;
g. Inactive fillers to filtrate the solid suspended material particles from the liquid substrate.

Processes in which such treating agents are applied, optionally while using clear or somewhat turbid liquid substrates, are known. Therefore, a detailed description of the usable granular treating agents is deemed unnecessary as such information is already known to those skilled in the art.

The particles of all granular treating agents should be solid in the sense that they would not be so greatly deformed under the flow pressure of the liquid substrate that the flow-through interstices would clog up. The particle diameter can be between 0.05 and 3 mm, especially between 0.2 and 1 mm. It is advantageous for the particles to be shaped as spherically as possible. Therefore, plastic particles producible by bead polymerization are especially suitable. However, granules made of mineral or ceramic materials, pressed or granulated powders, sintered or vitrified particles, metal pellets or the like can be used. In many cases porous or macroporous particles as discussed in detail for enzyme support particles play a special role.

The active ingredients required for the treatment of the liquid substrate themselves may form the body of the particles of the treating agent or they may be bound to the outer and/or inner surface of an otherwise inert particle.

The enzyme catalyst to be used for the preferred embodiment of the invention, namely whey hydrolysis, is described in detail below.

The Enzyme Catalyst

The enzyme catalyst contains as active ingredient a lactase, preferably of microorganisms, e.g. of Aspergillus varieties, such as *Aspergillus oryzae, Aspergillus niger,* of yeasts such as Saccharomyces, Kluyveromyces or of bacteria such as Stearothermophylus or *Escherichia coli.* The lactase is bound in a normal manner to a particle-shaped support. A method of the adsorptive bond of lactase, especially of *Escherichia coli,* to a hydrophobically modified support is described in DE-OS No. 28 39 737. For the covalent bonding, oxirane resin beads can be used to which the enzyme is bound by reaction with glycidyl groups. Suitable oxirane beads are described in DE-PS No. 22 37 316 and DE-PS No. 27 22 751. The lactase can also be first bound adsorptively and then can be cross-linked with a coupling component such as glutardialdehyde. Furthermore, immobilized cells of lactase-forming microorganisms can be used as enzyme catalyst.

The activity of the immobilized lactase should not be less than 100 lactase-U/g of moist support. The preferred activity range is between 200 and 400 U/g. One lactase-U is defined as that quantity of moist enzyme catalyst that sets free 1 $\mu$mole/min of glucose under standard conditions (30° C., pH=4.5) from a 5% lactase solution.

A multitude of organic or inorganic substances with a macroporous structure are suitable as supports for enzymes in general and lactase in particular. Such structures are substances with a pore volume of at least 1 ml/g and an average pore size of 1 to 500 nm. Supports with a hydrophilic, especially nonionic, matrix are preferred. The particle diameter can be between 0.1 and 1 mm, preferably 0.2 and 1.0 mm. A shape of the individual particles as spherical as possible is advantageous. Therefore, macroporous polymers producible by bead polymerization are especially suitable.

Examples of inorganic supports are ceramic pellets, macroporous glass or aluminum oxide. To produce binding sites for lactase, these supports can be silanized, for example by means of γ-aminopropyltriethoxysilane, to which the enzyme can be coupled by glutardialdehyde. Organic supports may consists of natural substances such as cork or corncob granules or macroporous plastics, such as acrylic resin, polystyrene, phenol formaldehyde resins and the like. Production processes for such macroporous substances are described, for example, in EP-A No. 58767. Support polymers with hydrophilic nonionic materix are obtained primarily by inverse bead polymerization of amides or hydroxyalkyl esters of acrylic or methacrylic acid.

The Turbid Liquid

The turbid liquid should have a viscosity not exceeding 1000 mPa in order to be able to flow through the fixed-bed reactor. The turbid liquids applied according to the invention contain finely divided solid matter which cause the turbidity. The degree of turbidity measured by the nephelometry method amounts to more than 10 NTU, preferably more than 100 NTU, as a rule about 200 to 700 NTU. The turbidity unit NTU (nephelometric turbidity unit) is also called JTU (Jackson turbidity unit) or FTU (formazine turbidity unit). Customary nephelometers (e.g., DRT-100 of Fisher Scientific Company) have already been calibrated for this unit. The temperature of the liquid can be between 0° and 60° C. depending upon the activity optimum of the immobilized lactase.

Even though it is not easy to provide a nephelometric upper limit for the process of the invention, it is restricted to the processing of "turbid" liquids in the usual meaning of the term. Liquid suspensions, slurries, pastes and the like that are already opaque in a thin layer belong to the turbid liquids processed according to the invention as little as do suspensions from which the solid matters precipitate after a short time. The maximum content of solid matters causing the turbidity depends upon the size of their particles and the setrling tendency in the fixed bed. Even turbid liquids with relatively high contents of solid matter are processible if the suspended particles from the fixed bed do not precipitate to a significant extent. Typical turbid liquids that are handled according to the process the invention are those that require cleansing of the fixed bed following a period of operation of at least 6 hours, preferably at least 12-24 hours or more. In extreme cases, cleansing may become necessary as early as after a 1 to 2-hour period of operation. The turbid liquids as a rule contain 0.1 to 50 g of suspended materials per liter.

Suspended materials may be organic or inorganic in nature and may be of natural or artificial origin. Organic suspended materials are, e.g., degradation products of plant, animal or microbial organisms, plant components in mashes and fruit juices, flocculations in animal blood, undissolved protein particles in protein hydrolysates, suspended materials in purified waste water, cellulose fibers in waste water of the paper industry, textile fibers in washing and cleansing liquids and latex particles made of natural or synthetic, optionally coagulated, latices. Argillaceous minerals, soot, dust or refinery slag from wet dust separators, or and stone particles and the like are among the inorganic suspended materials.

In the majority of the cases, the turbid liquids contain water or aqueous solutions as the liquid medium. An aqueous cleansing liquid may also be used. Other liquid media are, e.g., mineral oil, gasoline, chlorinated hydrocarbons, or other organic solvents. Besides the suspended solid material, the liquid medium may contain inorganic or organic substances in dissolved form, such as salts, fats, sugars, albumins and the like.

The invention is of special importance for the processing of whey. The whey used according to the invention is generally called "whole whey" in the industry to differentiate it from preheated and subsequently centrifuged wheys or permeate cleansed by ultrafiltration. Merely coarse flocculent or crumbly protein particles are separated prior to the processing. The remaining whole whey, which still contains 0.7 to 0.8% protein and 4.0 to 4.9% lactose, has a stable turbidity that cannot be removed by normal filters or by settling.

The Reactor

The reactor which is suitable for carrying out the process is described below in detail with an advantageous embodiment represented in FIG. 1 as a diagrammatic sectional view. It contains a reaction vessel 1 whose interior space is half filled at most, preferably 10 to 40% by volume, with a fixed bed 2 made of the particles of the granular treating agent. The interior space is divided from antechambers 5, 6 on two sides by sieve plates 3, 4. The size of the sieve plate openings is such that the particles of the treating agent cannot pass through. The reaction vessel, at least in the part in which the treatment of the fixed bed is arranged, preferably is cylindrically constructed. The other part 7 is filled only with the inflowing turbid liquids during the treatment. The sieve plates 3, 4 separate the antechambers 5, 6 from the reaction space. The volume of the antechambers is to be kept small. Conduits 8, 9, for introducing and removing liquids or gases, open into the antechambers. A significant characteristic of the reactor is the installation of fragmentation devices 10 approximately in the center. Insofar as they are stationary they can consist of a grid or grate made of rods covering the cross section of the reactor or a substantial part of it and are equipped with points or cutting edges in the direction of the fixed bed 2. All designs which split the fixed bed into fragments when it is pressed against them by hydrostatic pressure are suitable. Several fragmentation devices can be placed at various points of the free reactor space 7.

In a preferred embodiment, the fragmentation devices are movable so that they can make a movement crosswise of the longitudinal axis of the reactor or a movement that such a component has. If the fixed bed is pushed against the moved fragmentation device, at the beginning of the cleansing stage, the device engages the fixed bed, separates the particles from one another or splits the fixed bed into fragments which are further split up during fluidization. For example, a rotary shaft 11 with a majority of projecting blades 12 is suitable as a fragmentation device of this type. Shaft 11 is rotated by a drive 13 that is operated only at the beginning of the cleansing stage, whereby the blades 12 engage the uppermost layer of the fixed bed in each case. It is obvious that a multitude of similar rotary or swinging devices could fulfill the same purpose.

The fragmentation devices as a rule are so arranged in the reactor that at least in the fixed position they are placed outside the fluidized bed but optionally close above its surface.

Carrying out the Treatment Process

The turbid liquid is moved through the fixed bed so that it enters the fixed bed 2 from the free reactor space 7 and leaves it through the sieve plate 4. In this procedure, the direction of flow is preferably upward and the flow rate of the turbid liquid is so high that the particles of the treating agent are deposited in the upper part of the reactor in a fixed bed. If the flow rate is less than the sedimentation rate of the catalyst particles, then a downward flow is more advantageous.

In the case of whey hydrolysis, the hydrolysis conditions, such as time of direct contact, temperature, pH value or ion concentration, for example, largely depend on the properties of the immobilized enzyme. If a favorable choice of conditions is made, an 80-90% degree of hydrolysis can be maintained over a 12 to 24-hour period of operation per cycle.

Carrying out the Cleansing

In the interest of a uniformly high conversion, the cleansing stage is appropriately started before the activity of the treating agent noticeably declines. A 24-hour cycle has proven to be especially successful; this cycle is divided inro 18-22 hours of operation time and 2-6 hours of cleansing time. At the latest, the cleansing stage is started in each case when the activity has declined to less than 60% of the starting figure or the flow resistance of the fixed bed has doubled.

At the start of the cleansing stage, the flow of fresh turbid liquid is interrupted and a cleansing liquid is introduced instead. At first the turbid liquid still in the reactor can be displaced by water or any other substrate-free liquid without reversing the direction of flow. Thereafter, the direction of flow is reversed and an a cleansing liquid is introduced under pressure into the antechamber 6 from which the turbid liquid treated up to that time, e.g., the whey hydrolysate, was removed. It is a pressure that sets into motion the entire fixed bed in the reactor and presses it against the fragmentation devices. As soon as the fixed bed has completely passed the fragmentation devices and is split up, the drive of the fragmentation devices can be stopped. The treating agent, split into fragments of the fixed bed or into individual particles as much as possible, is now kept in a fluidized bed state for cleansing while the cleansing liquid constantly flows through the reactor. The direction of flow in the hydrolysis can agree with that of the turbidity; however, the flow rate must be so limited that the catalyst particles do not accumulate once again at the sieve plate, through which the cleansing liquid flows out, but remain fluidized. If the turbid liquid flows downward in the treatment stage, then the cleansing liquid can flow in the opposite direction, i.e., upward since at any rate this is the preferred direction of flow during the cleansing stage. Air blasts can be introduced into the flowing cleansing liquid to support the swirling.

Following conclusion of the cleansing there can be intermediate flushing, preferably in the direction of the flow of the turbidity, and then the introduction of the whey can again be started.

The Cleansing Liquid

The cleansing liquid, as a rule, consists of a substrate-free liquid which forms the liquid medium of the turbid liquid. At least it must be miscible with it. In the preferred case of the treatment of an aqueous turbid liquid, the cleansing liquid consists predominantly of water. As mentioned, pure water can be used before the start of the cleansing phase for the removal of the turbid liquid and likewise before the restarting of the treatment stage for removal of the cleansing liquid. Ordinary water can also be used for the process of splitting the fixed bed.

Pure water in most cases is not sufficient to cleanse the enzyme catalyst for the whey hydrolysis. A soluble protease can be added to degrade the deposited proteins. In its place or in addition surfactants can be added to the cleansing liquid. It is also possible to add first a cleansing liquid containing protease and then one containing a surfactant. Suitable as surfactants are nonionic but also cationic or anionically charged water-soluble surface-active substances such as petroleum sulfonates, polyethylene oxide derivatives or benzalkonium salts in a concentration of, e.g., 0.001 to 0.1%. During the cleansing process lasting several hours, the cleansing liquid preferably is constantly circulated. The flow rate in the reactor is adjusted so that the catalyst particles constantly remain in a fluidized state but the detached protein particles are carried away through the sieve plate with the cleansing liquid flowing off. The liquid is permitted to flow over a filter or a centrifugal separator and is redirected into the reactor by means of a pump. Instead a part of the cleansing liquid can constantly be drawn off and replaced by fresh liquid. If the flushing liquid is pure water, it is preferably pumped through once again.

Furthermore, it has been beneficial to add a disinfectant to the cleansing liquid to prevent infestation of the reactor and the catalyst with microorganisms. This preferably occurs following treatment with the cleansing liquid containing enzymes, but in any case only after the fluidizing of the catalyst particles. Suitable as disinfectants are, for example, hydrogen peroxide, peracetic acid or quaternary ammonium salts that optionally may have a surfactant effect at the same time. Tne disinfectants are used in an effective concentration and preferably are changed for each cycle to prevent accumulation of resistant germs. Correspondingly this also applied to the use of other enzyme catalysts and optionally to all processes in which there is danger of microbial infestation of the treating agent.

The present invention will be further illustrated by certain examples and references which are provided for purposes of ilustration only and are not intended to limit the same.

Example

A reactor corresponding to FIG. 1 made of transparent acrylic glass with an interior diameter of 8 cm and a height of 70 cm is filled with 1 kg of a commercial support-bound lactase made of *Aspergillus oryzae* (commercial name: Plexazym LA 1, Roehm GmbH). The enzyme catalyst has the following properties:
Beads, 0.5 mm average diameter
Electrically neutral matrix
Activity: 250 lactase-U/g humectant Sour whey from cottage cheese production is piped over this fixed bed daily for 20 hours. The sour whey has the following properties:
Dry content: 6.0–6.5%
Lactose content: 4–4.5%
pH=4.5
Turbidity: 650–700 NTU
No sedimentation of cheese powder in 24 hours at room temperature.

Because of the high rate of flow of 50 L/h, it is possible to build up a fixed bed at the upper end of the column in the case of an upward flow.

The following daily cleansing operation is undertaken following each 20 hours of hydrolysis operation.
1. Flushing out whey still present in the reactor with water;
2. Reversing the direction of flow of the water, splitting the fixed bed with the mechanical fragmentation device, if necessary repeatedly done with change in the direction of flow;
3. Building a fluidized bed while bubbling through air and piping through water upward at such a low speed that the beads do not accumulate into a fixed bed at the top of the reactor;
4. Removal of the suspended matters from the fluidized bed through 1 to 2 hours of flushing with water:
5. Substituting the water by a known disinfectant, e.g.
   a. 0.1% solution of a quaternary ammonium salt such as benzalkonium chloride (commercial name: Zephirol, Bayer AG)

b. 0.1% solution of H$_2$O$_2$
c. 0.1% formaldehyde solution
d. 0.1% acetic acid
e. 0.1% aqueous solution of a commercial protease (commercial name: Corolase A, Roehm GmbH)

The disinfectants or the protease solution a. to e. are changed every day. The solutions each are circulated for 30–60 minutes at room temperature. When the bacterial count is too high, two different disinfectants are flushed through, one after the other. Occasionally also heating to 50° C. for a short time takes place.

6. Flushing of the disinfectant with water for about 1 hour.

Result

The reactor was operated for 100 days in this manner. The degree of hydrolysis during the entire period and also at the end still was approximately 90% at the beginning of the daily cycle in question and 80–85% at the end of the cycle. During the entire period the support remained in the reactor and in each case was very free-flowing following completion of the cleansing operation.

Comparative Test

The same procedure as above was used but the mechanical fragmentation was omitted.

Result

After the 6th cycle the degree of hydrolysis had declined to 60%. The fixed bed could only be split once more by prolonged air injection, frequent reversing of the direction of flow.

After the 7th cycle, the fixed bed was clogged up and the degree of hydrolysis had declined to 30%. After opening the reactor, removing the support and a 5-hour cleansing in a separate container, comprising splitting, washing and disinfecting, the hydrolysis was restarted.

8th to 11th cycle: Undisturbed hydrolysis but declining degrees of hydrolysis.

12th cycle: Degree of hydrolysis declined to 40%. Clogging of the fixed bed. Renewed cleansing of the support outside the reactor. It was no longer possible to split the fixed bed completely into individual beads. The disinfection solution no longer reached the entire support surface.

13th to 15th cycle: Declining degree of hydrolysis, increasing clogging, increasing yeast growth, increasing pressure.

16th cyle: Support completely clogged, hydrolysis about 5%. Intensive cleansing and disinfection outside the reactor no longer resulted in a free-flowing fixed bed. The yeast was killed by means of a one-hour treatment of the support at 50° C.

17th cycle: After 20 hours of operation the fixed bed was completely clogged and could no longer be flowed through. Cleansing was no longer possible. The support had to be discarded.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for the continuous hydrolysis of lactose by the treatment of whey having turbidity in excess of 10 NTU with immobilized lactase without prior heating and centrifuging, which comprises flowing whey through a reactor containing a fixed bed of immobilized lactase comprising lactase immobilized on particles of a granular solid material, and periodically interrupting the flow of the whey and passing a flow of cleansing liquid through the fixed bed countercurrent to the flow of whey under sufficient hydrostatic pressure to press the fixed bed against moving fragmentation devices in the reactor to separate and fluidize the particles of the granular solid material into a fluidized bed whereby the particles containing immobilized lactase are cleansed by removing material deposited thereon from whey.

2. The process as in claim 1, wherein the cleansing liquid consists predominantly of water.

3. The process as in claim 1, wherein the cleansing liquid contains surface-active substances.

4. The process as in claim 2, which further comprises flushing prior to and following the flow of the cleansing liquid through the fixed bed.

5. The process as in claim 2, wherein said whey has a turbidity in excess of 100 NTU.

6. The process as in claim 5, wherein the cleansing liquid contains disinfectants.

7. The process as in claim 5, wherein the cleansing liquid contains a dissolved proteolytic enzyme.

8. The process as in claim 5 wherein said immobilized lactase has an activity of at least 100 u/g.

9. The process as in claim 1, wherein after the interruption of said whey flow, the whey which is still present in the packed bed is flushed away with water, thereupon said water is flushed away with the cleansing liquid, thereafter the cleansing liquid is flushed away by water.

10. The process as in claim 6, wherein said lactase is a lactase obtained from a microorganism selected from the group consisting of molds of the genus Aspergillus, yeast of the genus Saccharomyces or Kluyveromyces, bacteria of the genus Stearothermophylus and the bacteria species *Escherichia coli*.

* * * * *